United States Patent [19]

Takahashi et al.

[11] Patent Number: 4,636,456
[45] Date of Patent: Jan. 13, 1987

[54] PROCESS FOR FORMING A PHOTOGRAPHIC IMAGE

[75] Inventors: Toshiro Takahashi; Koki Nakamura, both of Kanagawa, Japan

[73] Assignee: Fuji Photo Film Co., Ltd., Kanagawa, Japan

[21] Appl. No.: 731,249

[22] Filed: May 7, 1985

[30] Foreign Application Priority Data

May 7, 1984 [JP] Japan .................................. 59-90435

[51] Int. Cl.$^4$ .............................................. G03C 5/24
[52] U.S. Cl. .................................... 430/266; 430/265; 430/267; 430/405; 430/949; 430/959; 430/485; 430/489; 430/957
[58] Field of Search ............................ 430/264–268, 430/566, 405, 949, 959, 485, 489, 957

[56] References Cited

U.S. PATENT DOCUMENTS

| 3,379,529 | 4/1968 | Porter et al. | 430/566 |
| 4,328,302 | 5/1982 | Nishimura et al. | 430/264 |
| 4,332,878 | 6/1982 | Akimura et al. | 430/264 |
| 4,377,634 | 3/1983 | Mifune et al. | 430/564 |

Primary Examiner—Won H. Louie
Attorney, Agent, or Firm—Sughrue, Mion, Zinn, Macpeak and Seas

[57] ABSTRACT

A process for forming photographic image is disclosed, comprising photographically developing, in the presence of a polyalkylene oxide compound, a silver halide photographic light-sensitive material including at least one silver halide emulsion layer and containing in at least said emulsion layer or other hydrophilic layer a compound represented by formula (I).

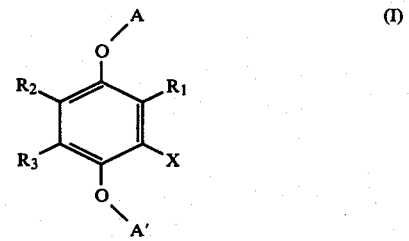

wherein:

A and A' each represents a hydrogen atom or an alkalihydrolyzable group;

$R_1$, $R_2$, and $R_3$ each represents a group capable of substituting a hydrogen atom on the hydroquinone nucleus, with $R_2$ and $R_3$, A and $R_1$, or A and $R_2$ together form a ring; and X represents a group which shows a development-inhibiting effect after being released.

13 Claims, 1 Drawing Figure

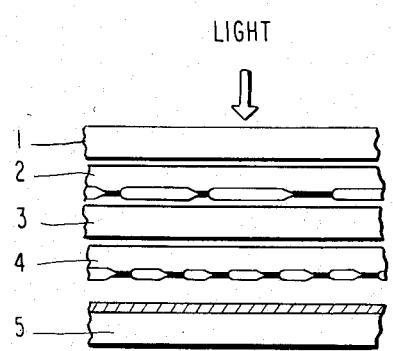

PROCESS FOR FORMING A PHOTOGRAPHIC IMAGE

FIELD OF THE INVENTION

This invention relates to a process for forming a photographic image with good halftone dot image quality using a silver halide photographic light-sensitive material, more particularly using a plate-making silver halide photographic light-sensitive material.

BACKGROUND OF THE INVENTION

It is known to form a photographic image with an extremely high contrast using a silver halide photographic light-sensitive material. As silver halide light-sensitive materials adapted for such purpose, lith type silver halide light-sensitive materials are known. In phtographic plate-making processes, continuous change in density of an original is usually converted to change in area of halftone dot by exposing through a contact screen. Therefore, tone reproducibility of the image is determined by tone of halftone dot image, or halftone gradation. In order to obtain high-quality prints with good tone reproducibility, it is necessary to realize a halftone gradation having a wide tone reproducibility of from minimum halftone dot area to maximum halftone dot area. In addition, long halftone gradation is useful for preventing deterioration of halftone gradation reproducibility due to optical blurring in the case of enlarging or reducing in size a halftone dot image using a camera. Another important quality of lith type silver halide light-sensitive materials as well as the tone reproducibility of halftone dot image is the quality of individual halftone dots constituting the halftone dot image. Points for evaluating halftone dot quality include sharpness, inking properties, and uniformity of halftone dots. In general, acceleration of development of a lith type light-sensitive material tends to shorten halftone gradation, although halftone dot quality is improved.

Techniques for lengthening the halftone gradation of lith type silver halide photographic light-sensitive material described hereinbefore, such as addition of a development-inhibiting compound to an emulsion layer, generally deteriorate halftone dot quality, and hence it is difficult to lengthen halftone dot gradation without deterioration of halftone dot quality. With respect to halftone dot quality, a problem exists with ordinary lith type silver halide photographic light-sensitive materials. That is, when halftone dot quality of the maximum dot is suitable, development of the minimum dots is somewhat inhibited, whereas when halftone dot quality of the minimum dots is suitable, development of the maximum dots becomes excessive. Thus, it is extremely difficult to obtain suitable halftone dot quality for both the minimum dots and the maximum dots.

SUMMARY OF THE INVENTION

Therefore, an object of the present invention is to provide a process for forming halftone dot images having non-contrasty halftone dot gradation without concurrent deterioration of halftone dot quality.

Another object of the present invention is to provide a process for forming halftone dot images composed of halftone dots all of which have suitable halftone dot quality.

A further object of the present invention is to provide a process for forming an image with high resolving power.

These and other objects of the present invention will become more apparent from the following description.

It has now been found that development of the maximum dots is depressed with almost no adverse influence on development of the minimum dots by incorporating in the lith type silver halide photographic light-sensitive material a compound capable of releasing a development inhibitor upon development in proportion to image density, and developing the light-sensitive material in the presence of a polyalkylene oxide compound, whereby the above-described defects are overcome, and light-sensitive materials with excellent properties are obtained.

Thus, the above-described and other objects of the present invention are attained by photographically developing, in the presence of a polyalkylene oxide compound, a silver halide photographic light-sensitive material including at least one silver halide emulsion layer and containing in at least one of said emulsion layer and other hydrophilic layer a compound represented by formula (I)

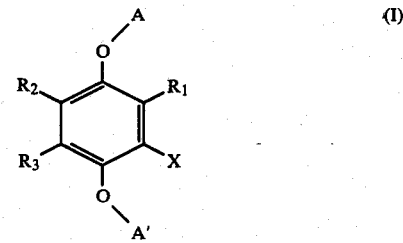

wherein:

A and A' each represents a hydrogen atom or an alkalihydrolyzable group;

$R_1$, $R_2$, and $R_3$ each represents a group capable of substituting the hydrogen atom of the hydroquinone nucleus, or $R_2$ and $R_3$, A and $R_1$, A and $R_2$, or A' and $R_3$ together form a ring; and X represents a group which shows a development-inhibiting effect upon being released (for example, in the step of development processing).

BRIEF DESCRIPTION OF THE DRAWING

The FIGURE illustrates a manner of forming letter images in a photographic plate-making process, wherein numeral 1 designates a transparent support, 2 a developed film (e.g., a line image original), 3 a transparent or semi-transparent pasting base, 4 a developed film (half-tone dot original), and 5 a light-sensitive material for reversion.

DETAILED DESCRIPTION OF THE INVENTION

Embodiments of formula (I) are described in further detail below.

Examples of the alkali-hydrolyzable group represented by A and A' include a substituted or unsubstituted acyl group (e.g., a chloroacetyl group, a dichloroacetyl group, etc.), an alkoxycarbonyl group having 2 to 10 carbon atoms in the alkoxy moiety (e.g., an ethoxy carbonyl group, etc.), an aryloxycarbonyl group having 6 to 10 carbon atoms in the aryloxy moiety (e.g., a phenoxycarbonyl group, etc.), etc.

$R_1$, $R_2$, and $R_3$ each represents a group capable of being substituted for a hydrogen atom on the hydroquinone nucleus, and, specifically, they may be the same or different and each represents a hydrogen atom, a substituted or unsubstituted alkyl group (preferably containing from 1 to 30 carbon atoms; e.g., a methyl group, an ethyl group, a t-butyl group, a t-octyl group, a dimethylaminomethyl group, a n-pentadecyl group, etc.), a substituted or unsubstituted aryl group (preferably containing from 6 to 30 carbon atoms; e.g., a phenyl group, a p-tolyl group, etc.), a substituted or unsubstituted alkylthio group (preferably containing from 1 to 30 carbon atoms; e.g., a n-butylthio group, a n-octylthio group, a sec-octylthio group, a tetradecylthio group, a 2-dimethylaminoethylthio group, etc.), a substituted or unsubstituted arylthio group (preferably containing from 6 to 30 carbon atoms; e.g., a phenylthio group, a 2-carboxyphenylthio group, a p-chlorophenylthio group, a 2-butoxy-5-t-octylphenylthio group, a 2-methoxycarbonylphenylthio group, etc.), a halogen atom (e.g., F, Cl, Br, I, etc.), a hydroxy group, a substituted or unsubstituted alkoxy group (preferably containing from 1 to 30 carbon atoms; e.g., a methoxy group, an ethoxy group, a benzyloxy group, an octyloxy group, a dodecyloxy group, etc.), a substituted or unsubstituted aryloxy group (preferably containing from 6 to 30 carbon atoms; e.g., a phenoxy group, a 4-carboxyphenoxy group, etc.), a substituted or unsubstituted acyl group (preferably containing from 1 to 30 carbon atoms; e.g., an acetyl group, a propionyl group, a benzoyl group, a chloroacetyl group, a 3-carboxypropionyl group, an octadecyloyl group, etc.), a substituted or unsubstituted alkoxycarbonyl group (preferably containing from 2 to 30 carbon atoms; e.g., a methoxycarbonyl group, an ethoxycarbonyl group, a phenoxycarbonyl group, an octadecyloxycarbonyl group, a methoxyethoxycarbonyl group, etc.), a substituted or unsubstituted amido group (preferably containing from 1 to 30 carbon atoms; e.g., an acetamido group, a propionamido group, a 3-carboxypropionamido group, a lauroylamido group, etc.), a substituted or unsubstituted sulfonamido group (preferably containing from 1 to 30 carbon atoms; e.g., a methanesulfonamido group, a p-toluenesulfonamido group, etc.), a substituted or unsubstituted carbamoyl group (preferably containing from 1 to 30 carbon atoms; e.g., a carbamoyl group, a butylcarbamoyl group, a 2-methoxyethylcarbamoyl group, an octylcarbamoyl group, a pyrrolidinocarbamoyl group, a morpholinocarbamoyl group, a hexadecylcarbamoyl group, etc.), a substituted or unsubstituted sulfamoyl group (preferably containing up to 30 carbon atoms; e.g., a sulfamoyl group, a dibutylsulfamoyl group, etc.), a substituted or unsubstituted sulfonyl group (preferably containing from 1 to 30 carbon atoms; e.g., a methanesulfonyl group, a benzenesulfonyl group, a p-dodecylbenzenesulfonyl group, etc.), and a heterocyclic ring group (e.g., a 5-tetrazolyl group, a 2-benzoxazolyl group, etc.); or X, $R_2$ and $R_3$, A and $A_1$, A and $R_2$, or A' and $R_3$ together form a ring.

X represents a group having a development-inhibiting effect, which is released when the compound represented by formula (I) is oxidized in the developing step, and examples thereof include substituted or unsubstituted benzotriazoles (specifically, benzotriazole, 5-nitrobenzotriazole, 5-methylbenzotriazole, 5-chlorobenzotriazole, 5-bromobenzotriazole, 5,6-dichlorobenzotriazole, 5-methoxybenzotriazole, 5-acetamidobenzotriazole, 5-phenoxycarbonyl benzotriazole, etc.), substituted indazoles (specifically, 5-nitroindazole, 5-chloroindazole, 5-nitro-6-chloroindazole, 4-nitroindazole, 6-nitroindazole, etc.), substituted benzimidazoles (specifically, 5-nitrobenzimidazole, 4-nitrobenzimidazole, 5,6-dichlorobenzimidazole, 5-chloro-6-cyanobenzimidazole, 5-chloro-6-trifluoromethylbenzimidazole, etc.), substituted or unsubstituted mercaptoazoles (specifically, 1-phenyl-5-mercaptotetrazole, 1-(4-carboxyphenyl)-5-mercaptotetrazole, 1-(3-hydroxyphenyl)-5-mercaptotetrazole, 1-(4-sulfophenyl)-5-mercaptotetrazole, 1-(4-sulfamoylphenyl)-5-mercaptotetrazole, 1-(3-hexanoylamidophenyl)-5-mercaptotetrazole, 1-(2-dimethylaminoethyl)-5-mercaptotetrazole, 1-ethyl-5-mercaptotetrazole, 1-(2-carboxyethyl)-5-mercaptotetrazole, 2-methylthio-5-mercapto-1,3,4-thiadiazole, 2-(2-carboxyethylthio)-5-mercapto-1,3,4-thiadiazole, 3-methyl-4-phenyl-5-mercapto-1,2,4-triazole, 2-mercapto-1,3-benzoxazole, 2-mercaptobenzimidazole, 2-mercapto-1,3-benzothiazole, 2-mercapto-1-phenylimidazole, 2-mercaptobenzothiazole, etc.), substituted or unsubstituted mercaptoazaindenes (specifically, 6-methyl-4-mercapto-1,3,3a,7-tetrazaindene, 6-methyl-2-benzyl-4-mercapto-1,3,3a,7-tetrazaindene, 6-phenyl-4-mercapto-1,3,3a,7-tetrazaindene, 4,6-dimethyl-2-mercapto-1,3,3a,7-tetrazaindene, etc.), substituted or unsubstituted mercaptopyrimidines (specifically, 2-mercaptopyrimidine, 2-mercapto-4-methyl-6-hydroxypyrimidine, 2-mercapto-4-propylpyrimidine, etc.), etc. These groups are preferably bound to the hydroquinone nucleus via the sulfur atom of the mercapto group or the nitrogen atom in the 1-position of the nitrogen-containing heterocyclic ring.

Specific examples of the compounds of the present invention represented by formula (I) are described below, which, however, is not intended to limit the scope of the present invention in any way.

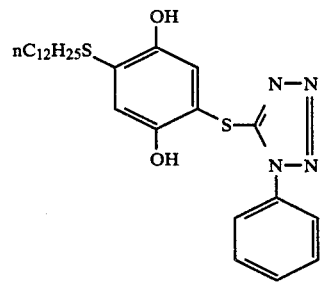

1.

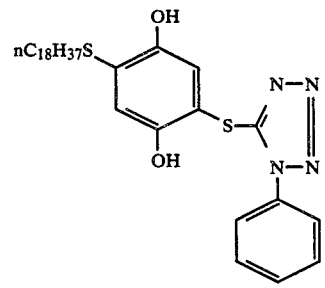

2.

-continued

-continued
13.
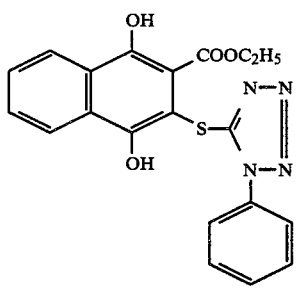
14.
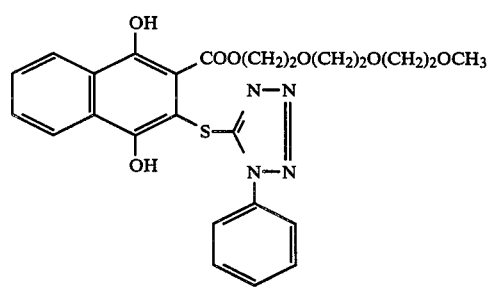
15.
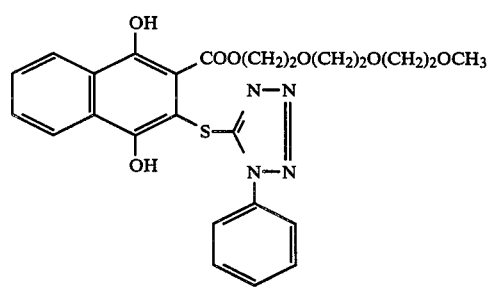
16.
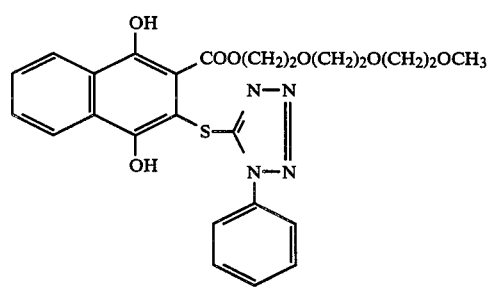
17.
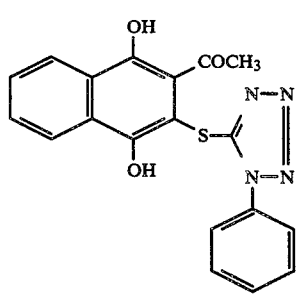
-continued
18.
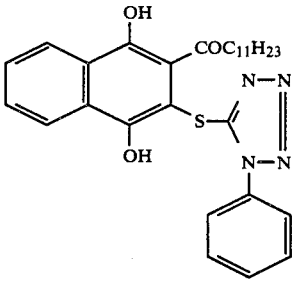
19.
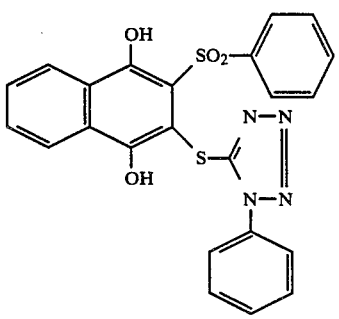
20.
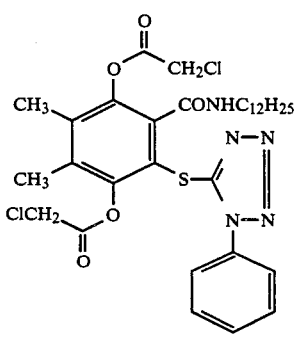
21.
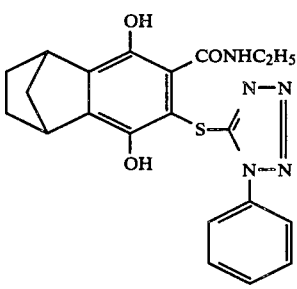
22.
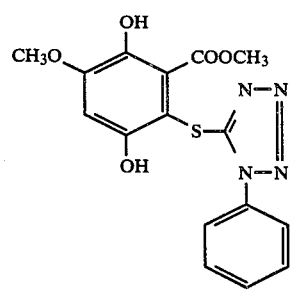

23.
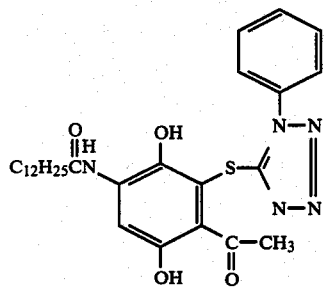
29.
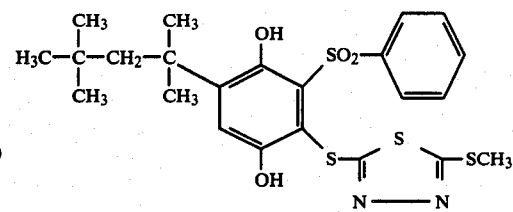
24.
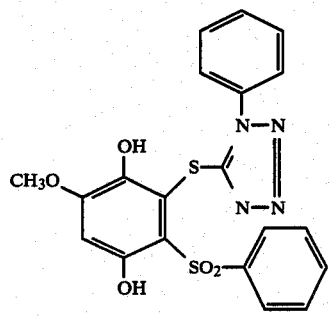
30.
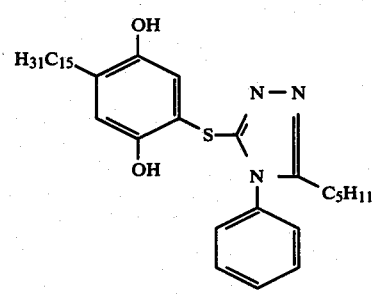
25.
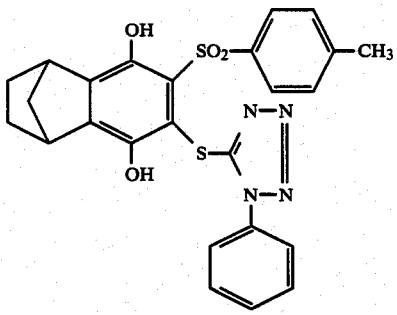
31.
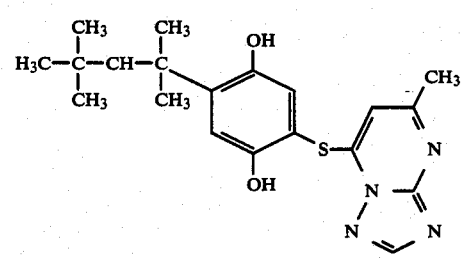
26.
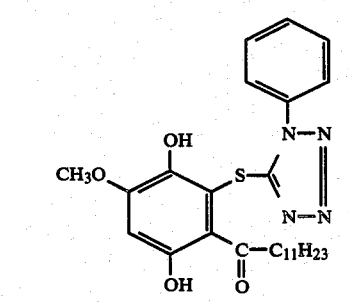
32.
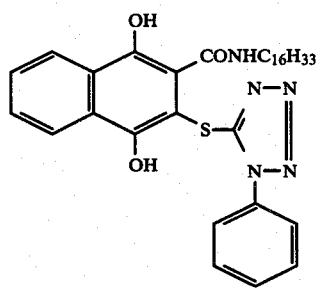
27.
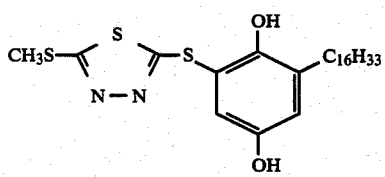
28.
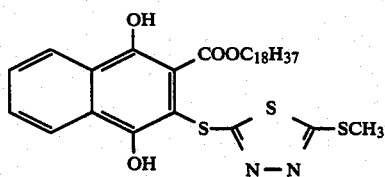
33.
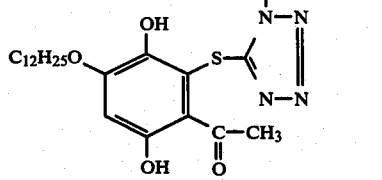

34.
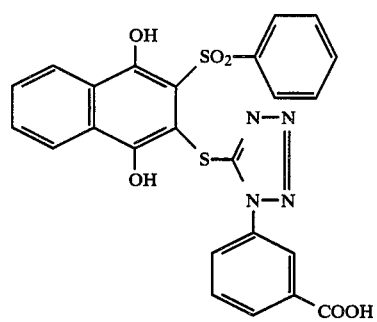
35.
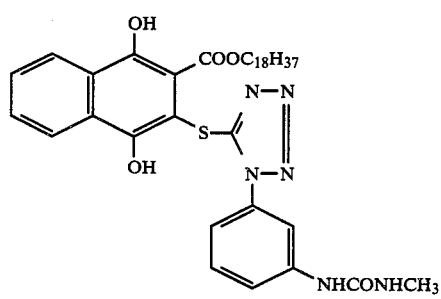
36.
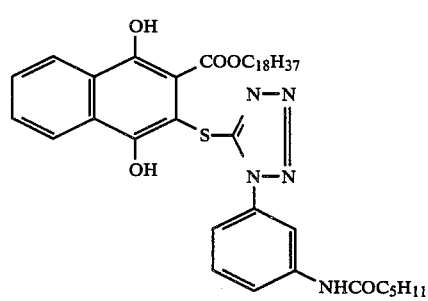
37.
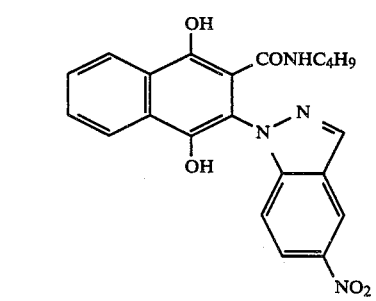
38.
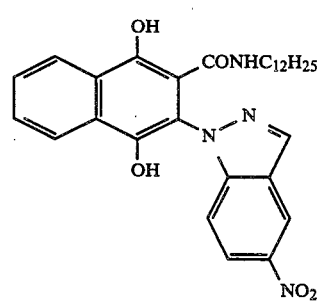
39.
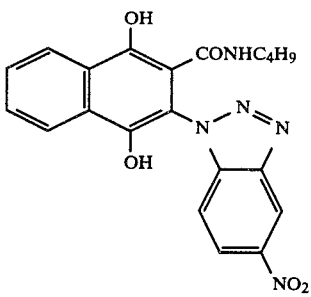
40.
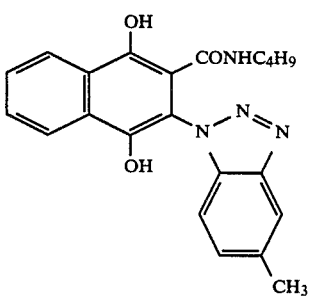
41.
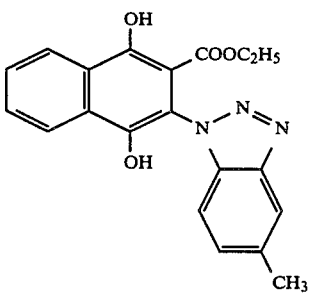
42.
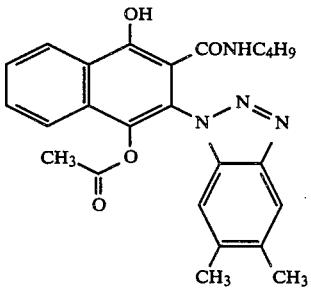
43.
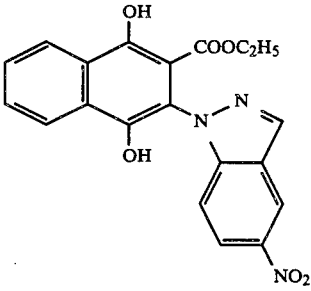

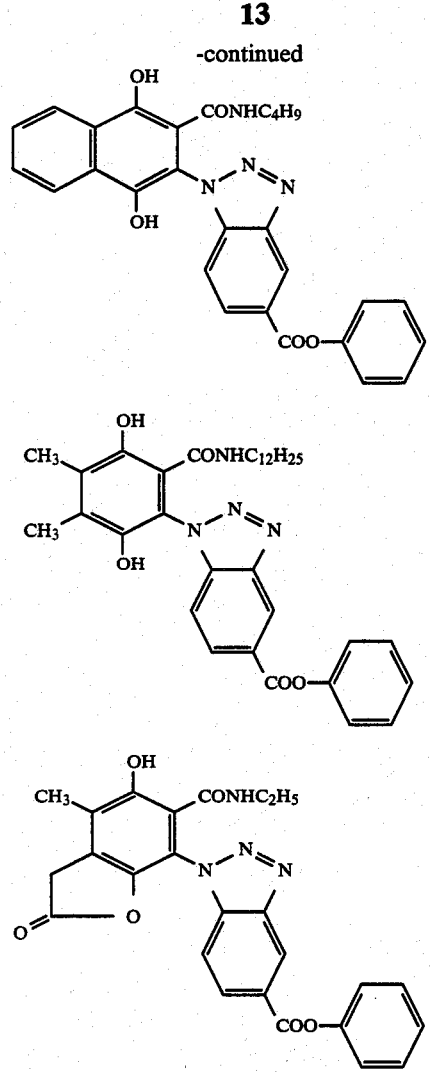

The compounds represented by formula (I) can be generally synthesized according to the following two process. One process comprises reacting a benzoquinone or naphthoquinone derivative with a development inhibitor at temperatures between room temperature and 100° C. in a halogenated carbon such as chloroform, 1,2-dichloroethane, carbon tetrachloride or methylchloroform in the presence of an acid catalyst such as p-toluenesulfonic acid, benzenesulfonic acid, methanesulfonic acid or trifluoromethanesulfonic acid. For example, compound examples 1, 2, 8, 29, 30, etc. described hereinafter can be synthesized by this process. Another process comprises reacting a benzoquinone or naphthoquinone derivative substituted by a chlorine atom, bromine atom or iodine atom with a development inhibitor at temperatures between −20° C. and 100° C. in an aprotic polar solvent such as acetone, tetrahydrofuran or dimethylformamide in the presence of a base such as potassium carbonate, sodium hydrogencarbonate or sodium hydride, and reducing the resulting quinone derivative with a reducing agent such as diethylhydroxylamine or sodium hydrosulfite. This process is suitable for synthesizing, for example, compound examples 10, 11, 21, 28, 44, etc., described hereinafter. (See: *Research Disclosure*, RD No. 18227 (1979); Liebigs Ann. Chem., 764, 131 (1972).

The benzoquinone or naphthoquinone derivatives to be used as starting materials can be synthesized, for example by processes as described in U.S. Pat. Nos. 2,899,334, 3,700,453, British Pat. Nos. 557,750 and 557,802, U.S. Pat. Nos. 3,043,690, 2,616,893, and 3,009,958, *Helv. Chem. Acta*, Vol. 30, 578 (1947), *J. Org. Chem.*, Vol. 22, 772 (1957), and references cited therein.

Indazole derivative-releasing DIR-hyroquinones, for example, compound examples 37, 38, and 39 described hereinafter can be synthesized, for example, by processes as described in Japanese Patent Application (OPI) Nos. 153,342/81 and 153,336/81.

Several examples of synthesizing the compounds are set forth below. The compounds to be used in the present invention may be easily synthesized by applying the exemplified processes.

SYNTHESIS EXAMPLE 1

Synthesis of compound 12

(1) Synthesis of 2-laurylcarbamoyl-1,4-dihydroxynaphthalene (1):

28 g of 2-phenoxycarbonyl-1,4-dihydroxynaphthalene was suspended in 150 ml of acetonitrile under a nitrogen stream, 22.2 g of laurylamine was dropwise added thereto, and the resulting mixture was refluxed for 4 hours. After completion of the reaction, the mixture was cooled, and crystals formed were collected by filtration. Yield: 26.8 g (72%).

(2) Synthesis of 3-chloro-2-laurylcarbamoyl-1,4-naphthoquinone (2):

7.4 g of compound (1) prepared above was added to 100 ml of chloroform, then stirred. 5.7 g of sulfuryl chloride was gradually added dropwise thereto while keeping the temperature of the solution at 5° to 10° C. After completion of the reaction, water was added thereto, followed by phase separation. The chloroform solution was separated, and, after distilling off the solvent, the residue was rapidly purified by column chromatography using silica gel with an element comprising 9 parts by volume of hexane and 1 part by volume of ethylacetate. Yield: 3.4 g (42%).

(3) Synthesis of 2-laurylcarbamoyl-3-(1-phenyl-tetrazol-5-ylthio)-1,4-naphthoquinone (3):

4 g of compound (2) prepared above was dissolved in 70 ml of acetone, and the resulting solution was cooled to 5° C. with ice-water.

2.1 g of 1-phenyl-5-mercaptotetrazole was added thereto, and 1.7 g of anhydrous potassium carbonate was added thereto, followed by stirring for 4 hours. Crystals precipitated were collected by filtration. For removal of inorganic substances, the crystals were further washed with 200 ml of a 10% aqueous solution of acetic acid, then dried. Yield: 3.5 g (55%).

(4) Synthesis of 2-laurylcarbamoyl-3-(1-phenyltetrazol-5-ylthio)-1,4-dihydroxynaphthalene (compound 12):

8.7 g of sodium hydrosulfite was dissolved in 80 ml or of water, and an acetonitrile solution of 5.5 g of compound (3) prepared above was added thereto at room temperature. Crystals were immediately formed, which were collected by filtration and recrystallized from ethyl acetate. Yield: 3.8 g (70%). m.p. 138°–140° C.

SYNTHESIS EXAMPLE 2

Synthesis of compound 34

(1) Synthesis of 2-phenylsulfonyl-1,4-dihydroxynaphthalene (4):

15.8 g of 1,4-naphthoquinone was dissolved in 100 ml of ethyl acetate/acetic acid (=9/1) at room temperature, and 24.6 g of sodium benzenesulfinate was added thereto. After stirring for 5 hours, crystals formed were collected by filtration, then washed with a small amount of acetone. Yield: 22.5 g (75%).

(2) Synthesis of 2-phenylsulfonyl-1,4-naphthoquinone (5):

10 g of compound (4) prepared above was suspended in 150 ml of acetone, and manganese dioxide was added thereto in an excess amount, followed by refluxing for 3 hours. Inorganic matter was removed by hot filtration, and the solvent was distilled off to obtain compound (5) as crystals. Yield: 4.5 g (45%).

(3) Synthesis of 2-phenylsulfonyl-3-[1-(3-carboxyphenyl)tetrazolyl-5-ylthio]-1,4-dihydroxynaphthalene (compound 3):

3 g of compound (5) prepared above and 2.1 g of 1-(3-carboxyphenyl)-5-mercaptotetrazole was suspended in 50 ml of ethyl acetate, and the suspension was refluxed for 2.5 hours under heating. Crystals thus formed were collected by filtration. Yield: 3.6 g (76%). m.p. 195°–197° C. (decomposition).

SYNTHESIS EXAMPLE 3

Synthesis of compound 43

(1) Synthesis of 2-ethoxycarbonyl-1,4-dihydroxynaphthalene (6):

28 g of 2-phenoxycarbonyl-1,4-dihydroxynaphthalene was dissolved in ethanol under a nitrogen stream, and 20.4 g of sodium ethylate was added thereto, followed by refluxing for 5 hours under heating. After being cooled, the solution was made weakly acidic with acetic acid, then ethanol was distilled off. Ethyl acetate and water were added thereto to separate and extract the product. The product was purified through silica gel column chromatography with an element having the same composition as that used in the Synthesis Example 1 to obtain compound (6) as crytals. Yield: 13 g (56%).

(2) Synthesis of 2-ethoxycarbonyl-3-chloro-1,4-naphthoquinone (7):

23 g of compound (6) prepared above was suspended in 300 ml of chloroform and, while keeping the solution at 5°–10° C., 27.4 g of sulfuryl chloride was slowly dropwise added thereto. After reacting for 1.5 hours, water was added to the reaction solution to conduct separation and extraction. The organic phase was dried with anhydrous sodium sulfate, and chloroform was distilled off under reduced pressure. Rapid purification of the residue through silica gel column chromatography gave compound (7) as crystals. Yield: 8.8 g (33%).

(3) Synthesis of 2-ethoxycarbonyl-3-(5-nitroindazol-1-yl)-1,4-naphthoquinone (8):

5.3 g of compound (7) was dissolved in 100 ml of acetone at room temperature, and 4.0 g of 5-nitroindazole was added thereto. Further, 3 g of anhydrous potassium carbonate was added thereto, and the resulting mixture was vigorously stirred for 5 hours. Crystals precipitated were collected by filtration under reduced pressure. The crystals were washed with 10% acetic acid for removing inorganic matter, then with a small amount of acetone, and then were dried. Yield: 4.3 g (51%).

(4) Synthesis of 2-ethoxycarbonyl-3-(5-nitroindazol-1-yl)-1,4-dihydroxynaphthalene (compound 43):

6.2 g of sodium hydrosulfite was dissolved in 80 ml of water, and a solution of 3 g of compound (8) prepared above in acetonitrile was added thereto. Crystals were immediately precipitated.

The crystals were collected by filtration, and recrystallized from methanol. Yield: 2.1 g (70%). m.p. 198°–200° C.

The compound represented by formula (I) is generally incorporated in a silver halide photographic light-sensitive material in an amount of from $10^{-7}$ to $10^{-1}$ mol/mol Ag, and preferably from $10^{-6}$ to $10^{-2}$ mol per mol of silver halide. However, the amount of the compound is not limited thereto and the compound represented by formula (I) may be used in a broader range.

Incorporation of the compound represented by formula (I) in a light-sensitive material may be effected in a manner conventionally employed for adding additives to a photographic emulsion. For example, water-soluble compounds may be added as an aqueous solution of a proper concentration, and water-insoluble or slightly water-soluble compounds may be added as a solution of a proper water-miscible solvent, which does not influence adversely on photographic properties, such as an alchol, a glycol, a ketone, an ester or an amide, to a photographic emulsion or a light-insensitive hydrophilic colloid solution. Also, an emulsifying and dispersing process well known for adding water-insoluble (called oil-soluble) couplers to an emulsion in the form of a dispersion may be employed.

In adding the compound of formula (I) to an emulsion layer by emulsification and dispersion, the compound is first dissolved in an organic solvent having a boiling point of about 180° C. or above such as an alkyl phthalate (e.g., dibutyl phthalate, dioctyl phthalate, etc.), trimellitic acid esters (e.g., tri-t-octyl trimellitate, etc.), phosphoric acid esters (e.g., diphenyl phosphate, triphenyl phosphate, tricresyl phosphate, dioctylbutyl phosphate, etc.), citric acid esters (e.g., tributyl acetylcitrate, etc.), alkylamides (e.g., N,N-diethyllaurylamide, etc.), or an organic solvent having a boiling point of about 30° C. to about 150° C. such as lower alkyl acetates (e.g., ethyl acetate, butyl acetate, etc.), ethyl propionate, sec-butyl alcohol, methyl isobutyl ketone, β-ethoxyethyl acetate, methylcellosolve acetate, etc., then dispersed in a hydrophilic colloid. The above-described high-boiling organic solvents and the low-boiling solvents may be used as a combination thereof.

The polyalkylene oxide compound to be used in the present invention together with the photographic development inhibitor-releasing compound represented by formula (I) may be added to either a silver halide photographic light-sensitive material, a developing solution, or both.

The polyalkylene oxide compound includes condensates between a polyalkylene oxide comprising at least 10 units of alkylene oxide containing 2 to 4 carbon atoms (e.g., ethylene oxide, propylene-1, 2-oxide, butylene-1, 2-oxide, etc., preferably ethylene oxide) and a compound having at least one active hydrogen atom (e.g., water, aliphatic alcohol, aromatic alcohol, fatty acid, organic amine, hexitol derivative, etc.), block copolymers of two or more different polyalkylene oxides, etc. Specifically, the following ones may be used as the polyalkylene oxide compounds:

polyalkylene glycols;
polyalkylene glycol alkyl ethers;
polyalkylene glycol aryl ethers;
polyalkylene glycol (alkylaryl) esters;
polyalkylene glycol esters;

polyalkylene glycol fatty acid amides;
polyalkylene glycol amines;
polyalkylene glycol block copolymers;
polyalkylene glycol graft polymers; etc.

As to molecular weight, polyalkylene oxides having a molecular weight of from 500 to 10,000 are preferably used.

Specific examples of the polyalkylene oxide compounds to be preferably used in the present invention are illustrated below.

Examples of useful polyalkylene oxide compounds include:

1.
1. $HO(CH_2CH_2O)_9H$
2. $C_{12}H_{25}O(CH_2CH_2O)_{15}H$
3. $C_8H_{17}CH{=}CHC_8H_{16}O(CH_2CH_2O)_{15}H$
4.

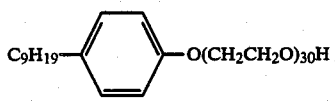

5. $C_{11}H_{23}COO(CH_2CH_2O)_{80}H$
6. $C_{11}H_{23}CONH(CH_2CH_2O)_{15}H$
7.

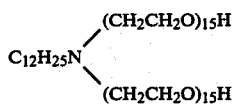

8. $C_{14}H_{29}N(CH_2)(CH_2CH_2O)_{24}H$
9.

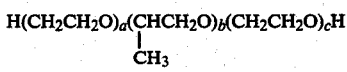

$$a + b + c = 50$$
$$b/a + c = 10/9$$

These polyalkylene oxide compounds may be used alone or in combinations of two or more.

In the case of adding the above-described polyalkylene oxide compound to a silver halide photographic light-sensitive material, the compound may generally be added in an amount of from $5 \times 10^{-4}$ g to 5 g, and preferably from $1 \times 10^{-3}$ g to 1 g, per mol of silver halide. In the case of adding the polyalkylene oxide compound to a developer, it may generally be added in an amount of from 0.1 g to 10 g per liter to developer.

Silver halides to be used in the light-sensitive silver halide emulsion layer of the present invention are not particularly limited, and silver chlorobromide, silver chlorobromoiodide, silver bromoiodide, etc., may be used, with silver chlorobromide or silver chlorobromoiodide containing at least 60 mol % (preferably 75 mol % or more) of silver chloride and 0 to 5 mol % of silver iodide being particularly preferable. Silver halide grains are not particularly limited as to form, crystal habit, size distribution, etc., but grains of 0.7 μm or less in size are preferable.

Sensitivity of the silver halide emulsion can be enhanced without coarsening grains, using a gold compound (e.g., chloroaurate, auric chloride, etc.), a salt of noble metal (e.g., rhodium, iridium, etc.), a sulfur compound capable of reacting with silver salt to form silver sulfate, or a reducing material (e.g., a stannous salt, an amine, etc.).

In addition, salts of noble metals such as rhodium, iridium, etc., or iron compounds such as red prussiate of potash may be present upon physical ripening or nucleus formation of silver halide grains.

As a hydrophilic colloid binder to be used in the present invention, gelatin is advantageously used, but other hydrophilic colloids may be used as well.

As gelatin, acid-processed gelatin or enzyme-processed gelatin as described in *Bull. Soc. Sci. Phot. Japan*, No. 16, p. 30 (1966) may be used, as well as lime-processed gelatin, and a gelatin hydrolyzate or an enzyme-decomposed product can be used.

For improving dimensional stability, physical properties of coatings, etc., a polymer latex comprising a homo- or copolymer of alkyl acrylate, alkyl methacrylate, acrylic acid, glycidyl acrylate or the like described in U.S. Pat. Nos. 3,411,911, 3,411,912, 3,142,568, 3,325,286, and 3,547,650, Japanese Patent Publication No. 5331/70, etc. may be incorporated in the silver halide emulsion layer or other layers.

The photographic emulsion to be used in the present invention may be orthomatically or panchromatically spectrosensitized or supersensitized using cyanine dyes such as cyanines, merocyanines or carbocyanines alone or in combination, or in further combination with styryl dyes.

Particularly, supersensitizing dyes described in Japanese Patent Application Nos. 20,623/75 and 93,833/75 and U.S. Pat. No. 3,567,458 are preferably used.

As antifoggants to be used in the photographic emulsion of the present invention, any antifoggant known in the art, such as various heterocyclic compounds (e.g., 4-hydroxy-6-methyl-1,3,3a,7-tetrazaindene, 3-methylbenzothiazole, 1-phenyl-5-mercaptotetrazole, etc.), mercury-containing compounds, mercapto compounds, etc. and those described in Japanese Patent Application (OPI) Nos. 81024/74, 6306/75, 19429/75, U.S. Pat. No. 3,850,639, etc., may be used.

The photographic emulsion of the present invention may contain inorganic or organic hardeners. For example, aldehyde compounds (e.g., mucochloric acid, formaldehyde, trimethylolmelamine, glyoxal, 2,3-dihydroxy-1,4-dioxane, 2,3-dihydroxy-5-methyl-1,4-dioxane, succinaldehyde, glutaraldehyde, etc.), active vinyl compounds (e.g., divinylsulfone, methylenebismaleimide, 1,3,5-triacryloyl-hexahydro-s-triazine, 1,3,5-trivinylsulfonylhexahydro-s-triazine, bis(vinylsulfonylmethyl)ether, 1,3-bis(vinylsulfonyl)-propanol-2, bis(α-vinylsulfonylacetamido)ethane, 1,2-bis(vinylsulfonyl)ethane, 1,1'-bis-(vinylsulfonyl)methane, etc.), active halogen compounds (e.g., 2,4-dichloro-6-hydroxy-s-triazine, etc.), ethylenediimine compounds (e.g., 2,4,6-triethyleneimino-s-triazine, etc.), etc., may be used alone or in combinations thereof.

To the photographic emulsion of the present invention may be added known surfactants other than polyalkylene oxides for aiding coating, preventing static charge, improving slipping properties and emulsion dispersion, preventing adhesion, improving photographic properties, and various other purposes. For example, natural surfactants (e.g., saponin, etc.), nonionic surfactants (e.g., glycidols, etc.), anionic surfactants having acidic group such as carboxylic acid group, sulfonic acid group (e.g., surfactants as described in U.S. Pat. No. 3,415,649), phosphoric acid group, sulfuric acid group, sulfuric ester group, phosphoric ester group, or the like, and amphoteric surfactants (e.g., amino acids, aminosulfonic acids, aminoalcohol sulfuric or phosphoric esters, etc.) are preferably used.

In the silver halide emulsion layer of the present invention, the weight ratio of the hydrophilic colloidal binder to silver halide is preferably ½ or less.

In the present invention, the silver halide emulsion layer is not necessarily composed of a single layer, but may be composed of two or more layer units. For example, in the case where the silver halide emulsion layer is composed of two layer units, it is more preferable to adjust the ratio of the sum of hydrophilic colloidal polymer to the sum of silver halide in the two layer units to ½ or less and incorporate a more amount of the hydrophilic colloidal binder in the upper light-sensitive emulsion layer than in the lower emulsion layer.

The silver halide is preferably coated in a silver amount of from 1.0 to 6.0 g/m².

In the light-sensitive upper layer of the present invention, a surfactant, an antistatic agent, a matting agent, a slipping agent, colloidal silica, a gelatin plasticizer, a polymer latex (e.g., that described in Japanese Patent Application No. 142,464/82), etc. may be used, as well as the above-described hydrophilic colloidal binder (e.g., gelatin).

As the matting agent, polymethyl methacrylate or silicon dioxide particles of from about 0.1 to 10 μm, and preferably from about 1 to 5 μm, in size are preferable.

As the support of the silver halide photographic light-sensitive material of the present invention, polyester films such as polyethylene terephthalate film and cellulose ester films such as cellulose triacetate film are preferably used.

In the present invention, exposure for obtaining image may be effected in a conventional manner. That is, any of known various light sources may be employed, such as natural light (sunlight), tungsten lamp, fluorescent lamp, mercury lamp, xenon arc lamp, carbon arc lamp, xenon flash lamp, flying spots on a cathode ray tube, etc. With respect to exposure time, not only can a short exposure time of 1/1,000 sec to one second employed for ordinary cameras be used, but an exposure time shorter than 1/1,000 second, for example, $1/10^4$ to $1/10^6$ second using a xenon flash lamp or a cathode ray tube may also be used; an exposure time longer than one second may be used as well. If necessary, spectral components of light to be used for the exposure may be adjusted using a color filter. Laser may also be used for exposure.

As a developing process to be used for forming photographic image in accordance with the present invention, there are a process of using a developer containing a developing agent, and a so-called alkali activator process which comprises previously incorporating a developing agent in a light-sensitive material and processing the light-sensitive material with an alkaline solution.

As the developing agent to be used for development processing in accordance with the present invention, those which are used for black-and-white development processing are preferable. For example, dihydroxybenzenes (e.g., hydroquinone, etc.), 3-pyrazolidones (e.g., 1-phenyl-3-pyrazolidone, etc.), aminophenols (e.g., N-methyl-p-aminophenol, etc.), 1-phenyl-3-pyrazolines, ascorbic acid, heterocyclic compounds wherein a 1,2,3,4-tetrahydroquinoline ring is fused with an indolene ring (e.g., as described in U.S. Pat. No. 4,067,872) may be used alone or as a combination thereof.

In addition, the developer generally contains known additives such as a preservative, an alkali agent, a pH buffer, an antifogging agent, and, if desired, the developer may further contain a dissolving aid, a toning agent, a development accelerator, a surface active agent, a defoaming agent, a water softener, a hardener, a thickening agent, etc.

The processing temperature is usually selected between about 18° C. and about 50° C. However, temperatures lower than about 18° C. or higher than about 50° C. may also be employed.

A so-called lith type developer is particularly preferably used in the present invention. This developer fundamentally comprises an o- or p-dihydroxybenzene, an alkali agent, a small amount of free sulfite salt, a sulfite ion buffer, etc. The o- and p-dihydroxybenzenes used as developing agents are properly selected from among those well known in the photographic field. Specific examples thereof include hydroquinone, chlorohydroquinone, bromohydroquinone, isopropylhydroquinone, toluhydroquinone, methylhydroquinone, 2,3-dichlorohydroquinone, 2,5-dimethyl-hydroquinone, etc.

Of these, hydroquinone is particularly useful. These developing agents may be used alone or in combination. They are generally added in amounts of from 1 to 10 g, and preferably from 5 to 80 g, per liter of the developer. The sulfite ion buffer is used in an amount sufficient to effectively keep the sulfurous acid salt concentration in the developer at an almost constant level. Examples thereof include aldehyde-alkali hydrosulfite adducts (e.g., formalin-sodium hydrogensulfite adduct, etc.), ketone-alkali hydrogensulfite adducts (e.g., acetone-sodium hydrogensulfite adduct, etc.), carbonylbisulfurous acid-amine condensates (e.g., sodium bis(2-hydroxyethyl)aminomethanesulfonate, etc.), etc. The sulfite ion buffer is used in an amount of 13 to 130 g per liter of the developer.

Alkali sulfites such as sodium sulfite may be added to the developer to be used in the present invention to thereby control the concentration of free sulfite ion. The sulfite is generally added in an amount of 5 g or less, and preferably 3 g or less, per liter of the developer, though it may of course be added in an amount of more than 5 g.

In many cases, incorporation of alkali halides (particularly, bromides such as sodium bromide, potassium bromide, etc.) as a development-adjusting agent is preferable. The alkali halide is added in an amount of from 0.01 g to 10 g, and preferably from 0.1 g to 5 g, per liter of the developer.

An alkali agent is added to the developer for adjusting pH of the developer to 9 or more (preferably from 9.7 to 12.5). Sodium carbonate or potassium carbonate is used in ordinary developers in various amounts.

As a fixing solution, those with a conventional composition may be used.

Suitable fixing agents include thiosulfates, thiocyanates and, in addition, organic sulfur compounds known as fixing agents can be used. The fixing solution may contain a water-soluble aluminum salt as a hardener. In forming dye images, conventional processes may be applied.

The development processing may be conducted manually or by means of an automatic developing machine. In the case of using an automatic developing machine, there are no limitations as to conveying method (for example, roller conveying, belt conveying, etc.), and conveying type automatic developing machines used in the art may be used. As to the formulation of processing solution and developing manner, reference may be made to U.S. Pat. Nos. 3,025,779, 3,078,024, 3,122,086, 3,149,551, 3,156,173, 3,224,356, 3,573,914, etc.

As to silver halide emulsion layers and other layers, supports, processing manner, etc., of the silver halide photographic light-sensitive material in accordance with the present invention, further reference may be made to Research Disclosure, Vol. 176, pp. 22-28 (Dec. 1978).

The present invention is now illustrated in greater detail by reference to the following examples which, however, are not to be construed as limiting the present invention in any way.

EXAMPLE 1

A silver halide emulsion comprising 80 mol % silver chloride, 19.5 mol % silver bromide, and 0.5 mol % silver iodide was prepared, and subjected to gold sensitization and sulfur sensitization in a conventional manner. This emulsion contained 45 wt. % of gelatin based on silver halide. After adding to this emulsion 3-carboxymethyl-5-[2-(3-ethyl-thiazolinylidene)ethylidene]rhodanine (spectral sensitizing agent), 4-hydroxy-1,3,3a,7-tetrazaindene (stabilizing agent), polyoxyethylene nonylphenyl ether containing 50 ethylene oxide units, and a polymer latex as described in U.S. Pat. No. 3,525,620, Preparation Example, Formulation 3,1,2-bis(-vinylsulfonylacetamido)ethane (hardener) was added in an amount of 2.6 wt % based on the total dry gelatin (i.e., total dry gelatin including gelatin of the light-insensitive upper layer to be described hereinafter). Further, each of the compounds of the present invention shown in Table 1 was added thereto as a methanol solution to prepare coating solutions for forming light-sensitive silver halide emulsion layers.

On the other hand, in parallel with the above-described procedure, sodium dodecylbenzenesulfonate (surfactant) and a polymethyl methacrylate latex (matting agent) of 3.0 to 4.0 $\mu$m in average particle size were added to a 5% gelatin solution to prepare a coating solution for forming a light-insensitive upper layer.

Then, the above-described coating solution for forming light-sensitive silver halide emulsion layer and the coating solution for forming light-insensitive upper layer were simultaneously coated on a polyester terephthalate support according to the method of coating two layers at the same time. Additionally, the amount of coated silver was 3.0 g/m$^2$, and the thickness of the light-insensitive upper layer was 1.0 $\mu$m. Thus, samples 1 to 14 were prepared.

A halftone dot image was formed on these samples in the following manner. That is, a commercially available negative gray contact screen (150 lines/inch) (produced by Dainippon Screen Co.) was closely superposed on each sample, and the sample was exposed to white tungsten light for 10 seconds through a step wedge having a step-to-step difference of 0.1. Then, each sample was developed at 27° C. for 100 seconds using the following developer, then fixed, washed and dried in a conventional manner.

Formulation of developer:
  Sodium carbonate (monohydrate): 50 g
  Formaldehyde-hydrogensulfite adduct: 45 g
  Potassium bromide: 2 g
  Hydroquinone: 18 g
  Sodium sulfite: 2 g
  5-Nitroindazole: 3 g
  Water to make: 1 liter Additionally, the comparative compounds set forth in Table 1 are as follows:

(Comparative compound (a): 1-Phenyl-5-mercaptotetrazole (Comparative compound (b): 5-Methylbenzotriazole (Comparative compound (c): 2-Methylthio-5-mercapto-1,3,4-thiadiazole.

Results of evaluating halftone dot quality and halftone gradation are tabulated in Table 1. Halftone dot quality was visually ranked in four grades, with "A" showing the best quality, "B" practical quality, "C" quality lower than practical limits, and "D" the worst quality. Halftone gradation is presented in Table 1 based on the difference in the logarithm of exposure amount providing a blacked area of 5% and that of 95%. The greater the difference, the less contrasty the halftone gradation.

TABLE 1

| Sample No. | Compound Structure | Added Amount | Halftone Dot Quality | Halftone Gradation |
|---|---|---|---|---|
| 1 | — | — | B | 1.13 |
| 2 | 10 | $2.6 \times 10^{-4}$ mol/mol Ag | A | 1.35 |
| 3 | 12 | $2.6 \times 10^{-4}$ mol/mol Ag | A | 1.33 |
| 4 | 13 | $2.6 \times 10^{-4}$ mol/mol Ag | A | 1.26 |
| 5 | 16 | $2.6 \times 10^{-4}$ mol/mol Ag | B | 1.35 |
| 6 | 21 | $2.6 \times 10^{-4}$ mol/mol Ag | A | 1.24 |
| 7 | 40 | $2.6 \times 10^{-4}$ mol/nol Ag | A | 1.25 |
| 8 | 28 | $2.6 \times 10^{-4}$ mol/mol Ag | A | 1.23 |
| 9 | Comparative Compound (a) | $6.5 \times 10^{-5}$ mol/mol Ag | C | 1.16 |
| 10 | Comparative Compound (a) | $1.3 \times 10^{-4}$ | D | 1.30 |
| 11 | Comparative Compound (b) | $6.5 \times 10^{-5}$ mol/mol Ag | C | 1.15 |
| 12 | Comparative Compound (b) | $1.3 \times 10^{-4}$ | D | 1.24 |
| 13 | Comparative Compound (c) | $6.5 \times 10^{-5}$ | C | 1.15 |
| 14 | Comparative Compound (c) | $1.3 \times 10^{-4}$ | D | 1.23 |

As is clear from Table 1, the compounds of the present invention show a very beneficial effect of making the halftone gradation less contrasty without deteriorating halftone dot quality. That is, where halftone gradation was made less contrasty by 0.1 or more using comparative compound (a), (b), or (c) than that of the sample of adding no such compounds, halftone dot quality was ranked "D". However, where the compounds of the present invention were added, the halftone gradation was made less contrasty by a difference of 0.1 to 0.2 more than that of the sample of adding such compounds, with halftone dot quality being ranked as high as "A" or "B".

EXAMPLE 2

$5\times10^{-3}$ mol of each of the compounds of the present invention shown in Table 2 was dissolved in a mixture of 4.0 ml of tricresyl phosphate and 15 ml of ethyl acetate, and the resulting solution was emulsified and dispersed in 100 g of a 10% gelatin aqueous solution using 0.3 g of sodium nonylbenzenesulfonate to prepare an emulsion.

Samples were prepared in the same manner as in Example 1, except for using the above-described emulsion in preparing coating solutions for forming light-sensitive silver halide emulsion layer in place of the methanol solution, then exposing and developing. Results thus obtained are shown in Table 2.

TABLE 2

| Sample No. | Compound Structure | Compound Added Amount | Halftone Dot Quality | Halftone Gradation |
|---|---|---|---|---|
| 15 | *Compound (I)-free emulsion | — | B | 1.16 |
| 16 | 10 | $5.2 \times 10^{-4}$ mol/mol Ag | A | 1.30 |
| 17 | 12 | $5.2 \times 10^{-4}$ mol/mol Ag | A | 1.28 |
| 18 | 14 | $5.2 \times 10^{-4}$ mol/mol Ag | B | 1.26 |

*Emulsion not containing compound (I) of the present invention.

It is seen from Table 2 that the compounds of the present invention also show the effect of making halftone gradation less contrasty when added in an emulsion form.

EXAMPLE 3

Samples 1, 2, and 6 in Example 1 were exposed and developed in the same manner as in Example 1 except that development processing was conducted in three different manners, i.e., at 27° C. for 90″, 100″, and 110″, respectively. Five-rank evaluation results of the halftone dot quality are shown in Table 3, with "5" showing the best quality, "1" showing the worst quality, and "5" to "3.5" being a practically employable range.

TABLE 3

| Sample No. | Compound | Halftone Dot % | Developing Time 90 sec. | 100 sec. | 110 sec. |
|---|---|---|---|---|---|
| 1 | — | 5 | 3.5 | 4.0 | 4.5 |
|  |  | 95 | 4.5 | 4.0 | 3.5 |
| 2 | 10 | 5 | 4.0 | 4.5 | 4.5 |
|  |  | 95 | 4.5 | 4.5 | 4.0 |
| 6 | 21 | 5 | 4.0 | 4.5 | 4.5 |
|  |  | 95 | 4.5 | 4.5 | 4.0 |

It is seen, from Table 3, that the halftone dot quality of the samples of the present invention was better than that of the compound-free sample with respect to both 5% and 95% halftone dots, and that the samples of the present invention provided good halftone dot quality when developed for a shorter of longer time than the standard developing time (100 seconds), thus having a wide developing latitude.

EXAMPLE 4

Samples 1, 2, 4, and 6 of Example 1 were exposed for 10 seconds to a white tungsten light using a plate-making camera through original (A) wherein 50-μm wide white lines were drawn against black background and original (B) wherein 50-μm wide black lines were drawn against white background, then developed in the same manner as described in Example 1. Results thus obtained are shown in Table 4.

TABLE 4

| Sample No. | Compound | Width (μm) of developed black lines using original (A) | Width (μm) of developed white lines using original (B) |
|---|---|---|---|
| 1 | — | 75μ | 30μ |
| 2 | 10 | 65μ | 40μ |
| 4 | 13 | 65μ | 40μ |
| 6 | 21 | 70μ | 38μ |

It is seen, from Table 4, that the compounds of the present invention provide good reproducibility of fine lines, which means, in an actual plate-making process, that a wide exposure latitude is provided for exposure to an original containing both Ming type letters and gothic type letters.

EXAMPLE 5

2-Hydroxy-4,6-dichloro-1,3,5-triazine sodium salt (hardener) and $1\times10^{-4}$ mol/mol Ag of polyoxyethylene nonylphenyl ether containing 30 ethylene oxide units were added to a silver halide emulsion comprising 95 mol % of silver chloride and 5 mol % of silver bromide and containing $1\times10^{-4}$ mol/mol Ag of rhodium, and each of the compounds of the present invention given in Table 5 was added as a methanol solution in an amount also shown in Table 5. Each of the resulting coating solutions was coated on a polyethylene terephthalate film in an amount of 4.5 g Ag/m². Each of the thus prepared film samples was exposed through an original having the structure shown in the FIGURE using a printer, Model P-607 made by Dainippon Screen Mfg. Co., Ltd., then developed at 38° C. for 20 seconds using the following developer, and fixed, washed with water, and dried in a conventional manner.

Formulation of developer
Potassium bromide: 2.0 g
Potassium hydroxide: 20 g
Potassium carbonate: 35 g
Potassium sulfite: 80 g
Hydroquinone: 20 g
Triethylene glycol: 30 g
Polyethylene glycol (m.w. 4000): 2.0 g
5-Nitroindazole: 0.1 g
Water to make: 1 liter (pH 11.7)

TABLE 5

| Sample No. | Compound Structure | Compound Added Amount | Letter Image Quality |
|---|---|---|---|
| 19 | — | — | 2 |
| 20 | 12 | $1.3 \times 10^{-4}$ mol/mol Ag | 5 |
| 21 | 13 | $1.3 \times 10^{-4}$ mol/mol Ag | 4 |

Letter image quality ranked 5 in Table 5 means that, when exposure is effected so that 50% halftone dot area of the original having the structure shown in the FIGURE is converted to 50% halftone area on a light-sensitive material for contact work 30-μm wide letters are reproduced, which means extremely good letter image quality. On the other hand, letter image quality ranked 1 means that, when the same exposure as described above is effected, only 150-μm wide or wider letters are reproduced, which means poor letter image quality. Ranks 4 to 2 were provided between 5 and 1, which was determined by organoleptic evaluation, with rank 2 or more being practically useful levels. That is, the grade of letter image quality formed under a condition under which a dot area of 50% is aptitudinally exposed on a reproduction film for contact work as a dot area of 50% using the original as shown in the FIGURE is determined with the following evaluation grades.

The grade 1: a letter having a width of broader than 150 μm is accurately reproduced.

The grade 2: a letter having a width of broader than 120 μm is accurately reproduced.

The grade 3: a letter having a width of broader than 90 μm is accurately reproduced.

The grade 4: a letter having a width of broader than 60 μm is accurately reproduced.

The grade 5: a letter having a width of 30 μm is accurately reproduced.

Any grade higher than 2 is at a practically usable level.

As is apparent from Table 5, the compounds of the present invention provides extremely superior letter image quality.

The terminology "letter images" means ink-free letters, symbols, etc., in portions where ink is disposed dotwise on paper (halftone dot portions) or in portions where ink is disposed all over (called solid portions) (refer to U.S. Pat. No. 4,452,882). A method for forming letter image in the photographic plate-making process is described in more detail below. As is shown in the FIGURE a developed halftone dot film (halftone dot original) 4 pasted on transparent or semi-transparent pasting base 3 (usually about 30 μm-thick polyethylene terephthalate film being used) is superposed on developed film (line image original) 2 having formed thereon so-called positive line image such as letter or symbol and being similarly pasted on pasting base 1, and the assembly is used as an original. An emulsion-coated side of reversing light-sensitive material 5 is contacted with the halftone dot image, and exposure and development are effected to thereby form white or cleared portions of the line image in the halftone dot image. An important point in this process is that the negative/positive image conversion of the halftone dot image and the line image must be effected in proportion to the dot area and the line width, respectively. For example, a halftone dot image having a black area of 50% must be accurately converted to a white area of 50%, and a line image having a black line width of 50 μm to a 50-μm wide white line. However, as is clear in the FIGURE, the halftone dot image is exposed by directly contacting with the emulsion side of the light-sensitive material for contact work, whereas the line image is exposed to the light-sensitive material via halftone dot original 4 (usually having a thickness of about 110 μm) and pasting base 3 (several-hundred μm thick) for the halftone dot original. That is, the line image is projected to the light-sensitive material for contact work as a blurred image through the several-hundred μm thick transparent or semi-transparent spacer. Thus, a typical exposure amount (enough to convert halftone dot area with good fidelity in a negative/positive manner) results in a thinner white line due to the blurring exposure. On the other hand, when the exposure amount is reduced so as to minimize the influence of blurring exposure and realize accurate negative/positive conversion of line image, halftone dot area is reduced due to lack of exposure. Thus, letter image quality is liable to be deteriorated.

While the present invention has been described in detail and with reference to specific embodiments thereof, it is apparent to one skilled in the art that various changes and modifications can be made therein without departing from the spirit and the scope of the present invention.

What is claimed is:

1. A process for forming a photographic image, comprising:

(1) imagewise exposing a silver halide photographic light-sensitive material including at least one silver halide emulsion layer and containing in at least said emulsion layer or other hydrophilic layer a compound represented by formula (I)

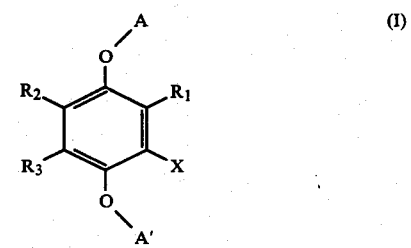

wherein:

A and A' each represents a hydrogen atom or an alkalihydrolyzable group;

$R_1$, $R_2$, and $R_3$ each represents a hydrogen atom or group capable of substituting a hydrogen atom on the hydroquinone nucleus, or $R_2$ and $R_3$, A and $R_1$, or A and $R_2$ together form a ring, wherein said ring is a 5-6 membered ring; and X represents a group which shows a development-inhibiting effect after being released, and (2) photographically developing the resulting imagewise exposed silver halide photographic light-sensitive material, using a lithographic developer, wherein a polyalkylene oxide compound is employed in said silver halide photographic light-sensitive material, or said lithographic developer or both.

2. A process for forming a photographic image as in claim 1, wherein

A and A' each represents a member selected from a hydrogen atom, a substituted or unsubstituted acyl group, an alkoxycarbonyl group, and an aryloxycarbonyl group;

$R_1$, $R_2$, and $R_3$ each represents a member selected from a hydrogen atom, a substituted or unsubstituted alkyl group, a substituted or unsubstituted aryl group, a substituted or unsubstituted alkylthio group, a substituted or unsubstituted arylthio group, a halogen atom, a hydroxy group, a substituted or unsubstituted alkoxy group, a substituted or unsubstituted aryloxy group, a substituted or unsubstituted acyl group, a substituted or unsubstituted alkoxycarbonyl group, a substituted or unsubstituted amido group, a substituted or unsubstituted sulfonamido group, a substituted or unsubstituted carbamoyl group, a substituted or unsubstituted sulfamoyl group, a substituted or unsubstituted sulfonyl group, and a heterocyclic ring group, a group represented by X, or $R_2$ and $R_3$, A and $A_1$, A and $R_2$ or A' and $R_3$ together form a ring, X representing a group which shows a development inhibiting effect after being released.

3. A process for forming a photographic image as in claim 2, wherein X is selected from a substituted or unsubstituted benzotriazole, a substituted indazole, a substituted benzimidazole, a substituted or unsubstituted mercaptoazole, a substituted or unsubstituted mercaptoazaindene, and a substituted or unsubstituted mercaptopyrimidine.

4. A process for forming a photographic image as in claim 1, wherein the compound represented by formula (I) is incorporated in the silver halide photographic light-sensitive material in an amount of from $10^{-7}$ to $10^{-1}$ mol per mol of silver halide.

5. A process for forming a photographic image as in claim 2, wherein the compound represented by formula (I) is incorporated in the silver halide photographic light-sensitive material in an amount of from $10^{-7}$ to $10^{-1}$ mol per mol of silver halide.

6. A process for forming a photographic image as in claim 3, wherein the compound represented by formula (I) is incorporated in the silver halide photographic light-sensitive material in an amount of from $10^{-7}$ to $10^{-1}$ mol per mol of silver halide.

7. A process for forming a photographic image as in claim 1, wherein the polyalkylene oxide is incorporated in the silver halide photographic light-sensitive material in an amount of from $5 \times 10^{-4}$ g to 5 g per mol of silver halide.

8. A process for forming a photographic image as in claim 2, wherein the polyalkylene oxide is incorporated in the silver halide photographic light-sensitive material in an amount of from $5 \times 10^{-4}$ g to 5 g per mol of silver halide.

9. A process for forming a photographic image as in claim 3, wherein the polyalkylene oxide is incorporated in the silver halide photographic light-sensitive material in an amount of from $5 \times 10^{-4}$ g to 5 g per mol of silver halide.

10. A process for forming a photographic image as in claim 4, wherein the polyalkylene oxide is incorporated in the silver halide photographic light-sensitive material in an amount of from $5 \times 10^{-4}$ g to 5 g per mol of silver halide.

11. A process for forming a photographic image as in claim 5, wherein the polyalkylene oxide is incorporated in the silver halide photographic light-sensitive material in an amount of from $5 \times 10^{-4}$ g to 5 g per mol of silver halide.

12. A process for forming a photographic image as in claim 6, wherein the polyalkylene oxide is incorporated in the silver halide photographic light-sensitive material in an amount of from $5 \times 10^{-4}$ g to 5 g per mol of silver halide.

13. A process for forming a photographic image as in claim 1, wherein said 5- or 6-membered ring is a napthalene ring, a bridged compound ring or a heterocyclic ring together with a moiety of

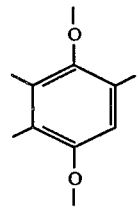

in formula (I).

* * * * *